United States Patent [19]

Osanai

[11] Patent Number: 4,768,158
[45] Date of Patent: Aug. 30, 1988

[54] APPARATUS AND METHOD FOR DIAGNOSING DETERIORATION OF SMOKESTACK

[75] Inventor: Takahito Osanai, Tokyo, Japan
[73] Assignee: Kajima Corporation, Tokyo, Japan
[21] Appl. No.: 6,123
[22] Filed: Jan. 23, 1987

[30] Foreign Application Priority Data

Jan. 25, 1986 [JP] Japan .................................. 61-13001

[51] Int. Cl.$^4$ ...................... G06F 15/32; G01N 25/72
[52] U.S. Cl. ................................... 364/507; 364/557; 374/5; 374/124
[58] Field of Search ...................... 374/124, 137, 4, 5; 364/557, 507

[56] References Cited

U.S. PATENT DOCUMENTS

| | | | |
|---|---|---|---|
| 4,343,182 | 8/1982 | Pompei | 374/186 X |
| 4,413,324 | 11/1983 | Tatsuwaki et al. | 364/557 |
| 4,452,538 | 6/1984 | Reger et al. | 374/124 |
| 4,671,674 | 6/1987 | Detronde | 374/124 X |

FOREIGN PATENT DOCUMENTS 58-124938  7/1983  Japan .................................. 374/4

Primary Examiner—Daniel M. Yasich
Attorney, Agent, or Firm—Oblon, Fisher, Spivak, McClelland & Maier

[57] ABSTRACT

The disclosed apparatus and method diagnose deterioration of a steel-reinforced concrete smokestack by taking its infrared ray photograph, thermographically processing the photograph into an outside surface temperature distribution diagram so as to detect a defect as a singular point on the diagram, measuring the circumferential length (L) of the defect from the diagram, finding concrete crack width (W) at the defect based on outside surface temperature difference between sound portion of the smokestack and the defect, and calculating reduction of the strength of the smokestack wall structure due to the defect by using the circumferential length (L) and the concrete crack width (W) of the defect.

5 Claims, 4 Drawing Sheets

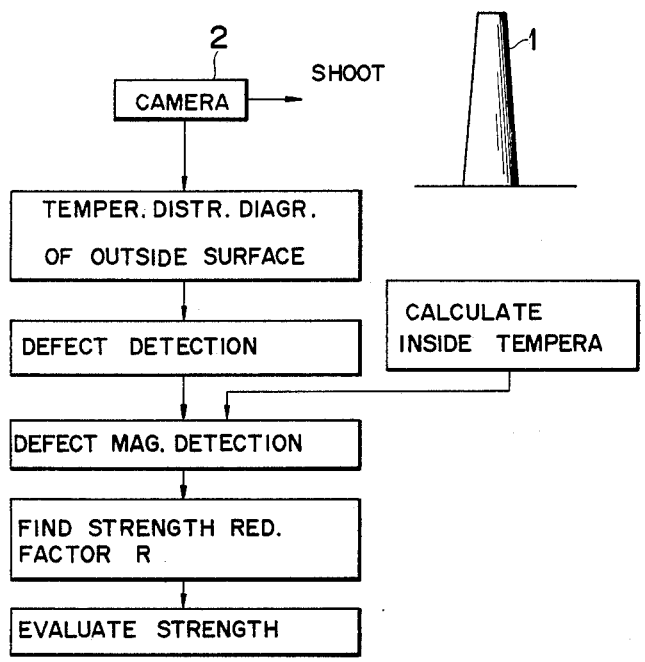
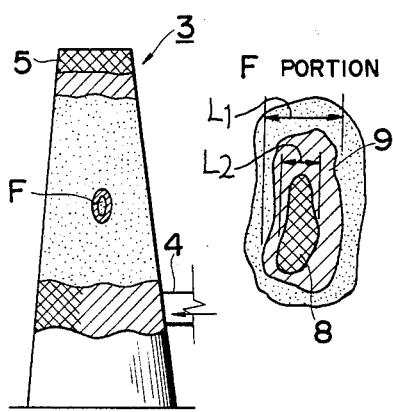
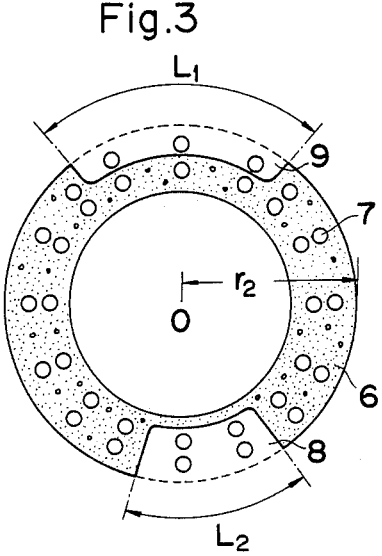

APPARATUS AND METHOD FOR DIAGNOSING DETERIORATION OF SMOKESTACK

BACKGROUND OF THE INVENTION

1. Field of the Invention

This invention relates to an apparatus and a method for diagnosing deterioration of a steel-reinforced concrete (to be referred to as "SRC", hereinafter) smokestack (sometimes, an SRC smokestack will be referred to as a smokestack), and more particularly to an apparatus and a method for non-destructive diagnosis of defects of an SRC smokestack without any direct contact therewith.

2. Description of the Prior Art

SRC smokestacks are directly exposed to corrosive environment; namely, severe meteorological conditions, and corrosive substances such as industrial wastes and various exhaust gases. The intermittent passages of hot smoke through the inside of the smokestacks results in repeated temperature variations over a wide range. The repeated wide-range temperature variation in the corrosive environment tends to accelerate deterioration of the structural material, at least partially, after service for a long period of time, and in the worst case, there is a risk of collapse which might seriously affect the circumstances. However, there is no practicable method available for non-destructive diagnosis of the SRC smokestack for the risk of collapse without interrupting its operation.

SUMMARY OF THE INVENTION

Therefore, an object of the present invention is to provide an apparatus and a method for non-destructive diagnosis of deterioration of SRC smokestacks. To fulfil this object, the invention uses a combination of thermography, temperature distribution analysis through the smokestack, and strength reduction evaluation.

To begin with, the outside surface of an SRC smokestack is photographed by an infrared ray camera, and a diagram of outside surface temperature distribution is prepared by thermographically processing the infrared ray photograph of the smokestack. Preferably, the smokestack is photographed from four different directions, e.g., from north, south, east, and west of it, so as to produce an outside surface temperature distribution diagram which covers the entire outside surface of the smokestack. At a defect, the temperature distribution becomes discontinuous, and a singular phenomenon in the temperature distribution is noticeable at the defect. Thus, one can find such defect of the SRC smokestack by scanning the outside surface temperature distribution diagram so as to locate a singular point where the singular phenomenon exists.

Temperature distribution in the SRC smokestack is analyzed based on the temperature of smoke at the inlet of the smokestack, the above-mentioned outside surface temperature distribution, thermal characteristics of the smokestack structure, and the ambient conditions. As a result, temperature difference between inside and outside of the SRC smokestack at the defect is determined. A means is provided for determining length of the defect in the height direction of the smokestack, i.e., a concrete crack width W, based on the temperature difference thus determined and thermal characteristics of the smokestack wall.

The circumferential length L of the defect can be measured from the above-mentioned outside surface temperature distribution diagram. A reduction factor R of the yield strength of the SRC smokestack is calculated for each defect from the information on the defect thus found. Preferably, the concrete crack width W and the circumferential length L of the defect are used to determine the reduction factor R. Finally, strength of the smokestack, e.g., strength against seismic loading, is evaluated or diagnosed by using the reduction factor R of the yield strength for all the defects located.

BRIEF DESCRIPTION OF THE DRAWING

FIG. 1 is a schematic block diagram of an apparatus for diagnosing deterioration of smokestack according to the invention;

FIG. 2 is an explanatory illustration of an outside surface temperature distribution diagram to be used in the apparatus and the method of the invention;

FIG. 3 is a diagrammatic sectional view of a smokestack which illustrates the circumferential length L of a defect;

Like parts are designated by like numerals and symbols throughout different views of the drawings.

DESCRIPTION OF THE PREFERRED EMBODIMENT

Referring to FIG. 1 and FIG. 2, the outside surface of an SRC smokestack 1 is photographed by an infrared ray camera 2. An outside surface temperature distribution diagram 3 is prepared by thermographically processing the infrared ray photographs taken by the camera 2. A fault F is located by scanning the outside surface temperature distribution diagram 3 so as to find a temperature-discontinuous spot therein as described in the foregoing.

Figure 6:
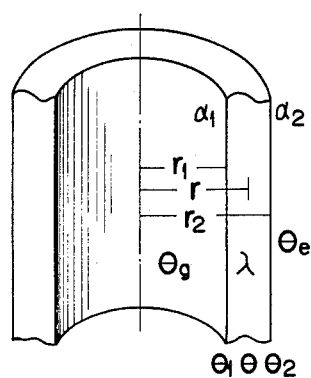
FIG. 6 is a fragmentary perspective view of a smokestack wall which shows nomenclatures to be used in the temperature analysis in the smokestack.

A method for determining the temperature distribution in the SRC smokestack 1 will be described by referring to FIG. 6. In the case of a hollow concrete cylinder, the relationship between temperatures of inside and outside gases and the temperature of the cylindrical wall is given by the following equations.

The inside surface temperature $\theta_1$ is $$\theta_1 = \theta_g - (K/\alpha_1 r_1)(\theta_g - \theta_o) \quad (1)$$

The outside surface temperature $\theta_2$ is $$\theta_2 = \theta_o + (K/\alpha_2 r_2)(\theta_g - \theta_o) \quad (2)$$

Temperature in the cylindrical wall $\theta$ is $$\theta = \theta_1 - (\theta_1 - \theta_2)\frac{\ln(r/r_1)}{\ln(r_2/r_1)} \qquad (3)$$

Here, $$(1/K) = (1/\alpha_1 r_1) + (1/\alpha_2 r_2) + (1/\lambda)\ln(r_2/r_1)$$

The temperature difference between inside and outside of the smokestack wall $\Delta\theta$ is $$\Delta\theta = (K/\lambda)\ln(r_2/r_1)\cdot(\theta_g - \theta_o) \qquad (4)$$

Here,
- $r_1$: inside radius (m)
- $r_2$: outside radius (m)
- $\theta_g$: smoke temperature (°C.)
- $\theta_o$: outside air temperature (°C.)
- $\alpha_1$: inside surface coefficient of heat transfer, value found from record
- $\alpha_2$: outside surface coefficient of heat transfer, value found from record
- $\lambda$: coefficient of heat transfer of concrete
- $K$: coefficient of overall heat transmission, calculated value When constants for a specific SRC smokestack 1, i.e., $r_1$, $r_2$, $\lambda$, $K$, $\alpha_1$, $\alpha_2$, and the outside air temperature $\theta_o$ are given, if the smoke temperature $\theta_g$ at the inlet 4 of the smokestack 1 is measured by a suitable means, the smoke temperature $\theta_g$ at the top 5 of the smokestack 1 can be determined by the above equation (2) after reading the outside surface temperature $\theta_2$ at the smokestack top 5 from the outside surface temperature distribution diagram 3. The inside surface temperature $\theta_1$ at the inlet 4 and the top 5 of the smokestack 1 can be determined by the equation (1) by using the thus determined smoke temperature.

Figure 4:
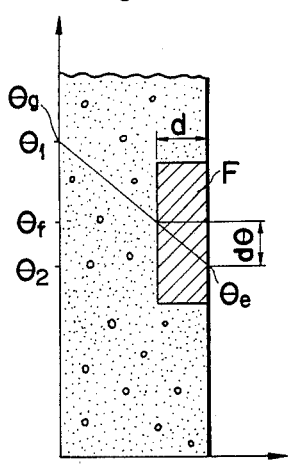
FIG. 4 is a fragmentary sectional view of a smokestack wall which illustrates temperature gradient therein.

A method for determining the magnitude of the defect F in the height direction of the smokestack 1, i.e., the concrete crack width W, will be described now by referring to FIG. 4 and FIG. 5. When the location of the defect F is detected, the inside surface temperature $\theta_1$ for the defect location can be calculated in the above-mentioned manner. The outside surface temperature $\theta_2$ at the surrounding of the defect F can be read from the outside surface temperature distribution diagram 3. Thus, the temperature distribution in the smokestack wall without any defect can be determined as shown in FIG. 4. In the outside surface temperature distribution diagram 3, if the defect outside surface temperature $\theta_f$ is higher than its surrounding by $d\theta$, the cause for such temperature difference may be attributed to the peeling off of a concrete layer of thickness d. Such thickness d can be easily calculated from the above temperature difference $d\theta$ and the temperature slope in the smokestack wall.

Figure 5:
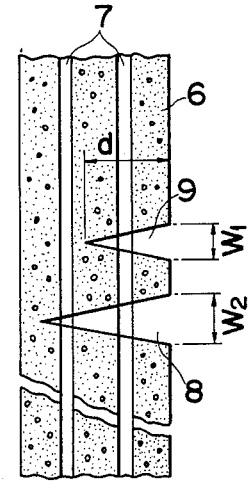
FIG. 5 is a fragmentary sectional view of a smokestack wall which illustrates the concrete crack width W of a defect.

In practice, there is a known empirical relationship between the depth d of the defect F and the concrete crack width W of FIG. 5. Accordingly, if the outside surface temperature difference $d\theta$ between the defect and the surrounding sound portion is found from the outside surface temperature distribution diagram 3, the concrete crack width W of such defect F can be empirically found from data collected by measurement of existing smokestacks.

The circumferential length $L_1$ and $L_2$ of the defects 8 and 9 of FIG. 3, taken in the direction of the circumference of the smokestack 1, can be determined by observation of the outside surface temperature distribution diagram 3. It is noted that a comparatively deep defect 8 of FIG. 2 is located within the comparatively shallow defect 9, but they are located at diametrically opposite positions of the smoke stack in FIG. 3.

Figure 7:
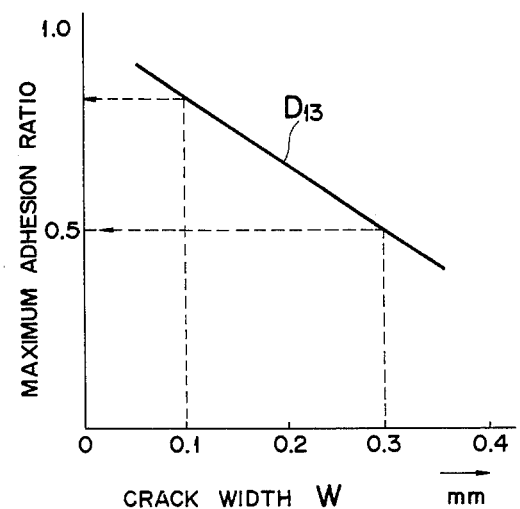
FIG. 7 is a graph showing the relationship between maximum adhesion ratio and the concrete crack width.

A method for determining the reduction factor R of the yield strength of the smokestack 1 due to the defect F will be described now. It is known that there is a correlation between the concrete crack width W and the maximum adhesion ratio of steel rod 7 to concrete 6, which correlation is shown in FIG. 7. For instance, in the case of steel rod of 13 mm diameter, for the concrete crack width W of 0.3 mm, the maximum adhesion ratio is reduced to 0.5, while for the concrete crack width W of 0.1 mm, the maximum adhesion ratio is about 0.8. Thus, once the concrete crack width W is found, the adhesion of the steel rod 7 to the concrete 6 can be estimated.

It should be noted here that, as far as the seismic strength of the SRC smokestack 1 is concerned, steel rods 7 which are not adhered to the concrete 6 do not contribute to structural strength judging from the strength against compression and pull-out. It may be safely assumed that the steel rod with a maximum adhesion ratio of 50% have a strength equivalent to one half of their strength with 100% maximum adhesion ratio.

Referring to FIG. 3, the illustrated smokestack 1 is assumed to have two concentric layers of reinforcing steel rods 7 with a spacing in the radius direction thereof, and the two layers of steel rods 7 are exposed to defects 8 and 9 of different degrees. A reduction factor R of the yield strength, as a fraction of the full strength with perfect adhesion of the steel rods 7 to the concrete 6, is determined by considering the circumferential lengths $L_1$, $L_2$ and the deterioration of the adhesion of the steel rods 7 to the concrete 6. For instance, in the case of FIG. 3, a reduction factor R is given by $$R = (0.5 p_1 L_1 + p_2 L_2)$$

here, $p_1$ is the maximum adhesion ratio of the defect 9 with a circumferential length $L_1$, and $p_2$ is the maximum adhesion ratio of the defect 8 with a circumferential length $L_2$.

In the present invention, it is checked whether the strength of the smokestack 1 after considering the above-mentioned reduction factor R of the yield strength can withstand the foreseeable seismic loading or not. If it can withstand, the smokestack 1 is diagnosed to be safe for continuous use, while if it cannot withstand, the smokestack 1 is diagnosed to be dangerous and repair or other suitable remedy is recommended.

Figure 8:
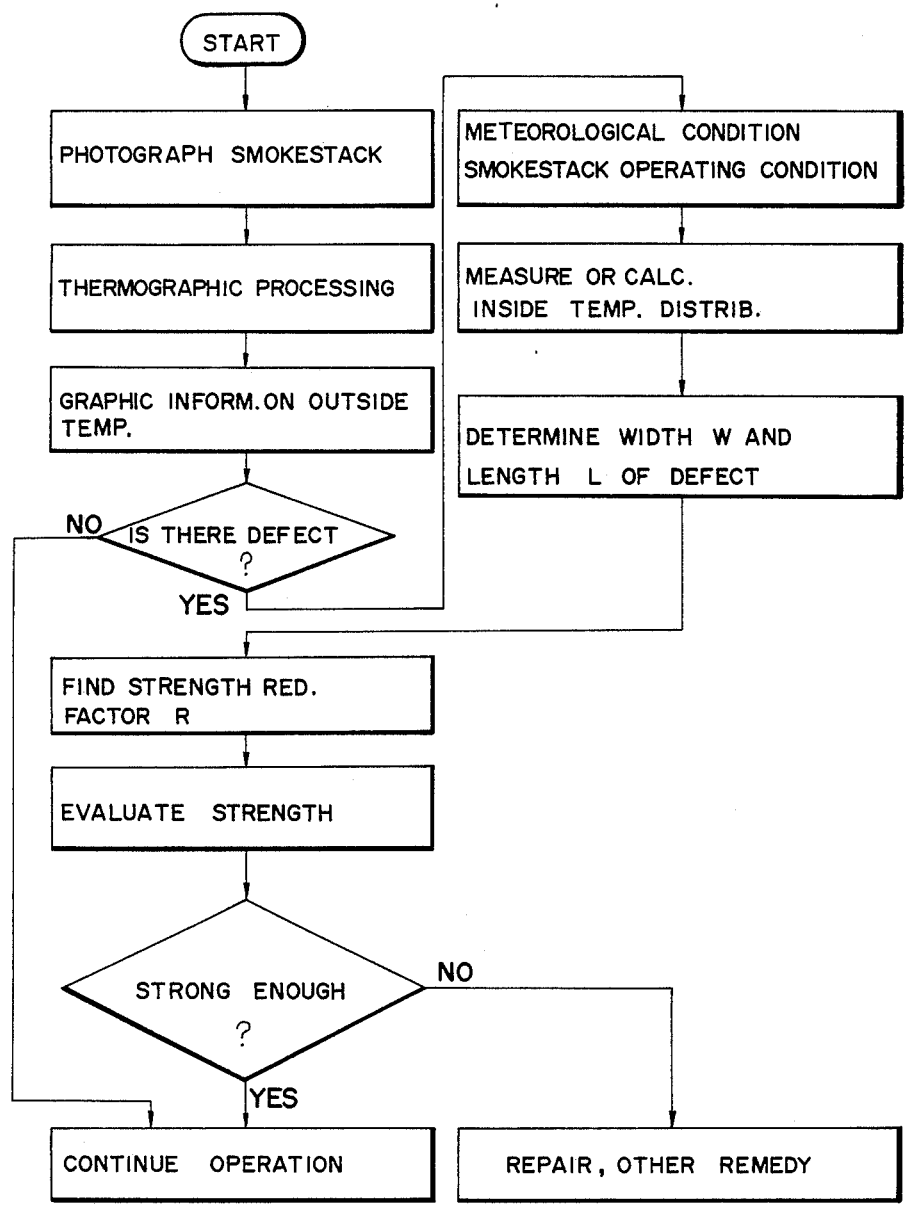
FIG. 8 is a flow diagram of the method for diagnosing deterioration of a smokestack according to the invention.

FIG. 8 shows the above diagnosing process in the form of a flow chart. As can be seen from the figure, the diagnosing process of the invention is suitable for execution by a computer program. Thus, the invention facilitates computerized diagnosis of smokestacks.

EXAMPLE

The diagnosing method of the invention was applied to a 30 m high SRC smokestack for detecting defects and checking the necessity of repair. The major constants of the smokestack were as follows.

Ground level (0 m from the ground)
  inside diameter: 1332 mm
  outside diameter: 2134 mm
  wall thickness: 401 mm Top portion (30 m above the ground)
inside diameter: 1000 mm
outside diameter: 1240 mm
wall thickness: 120 mm
Vertical steel rods for reinforcement
0–10 m above ground: 50 rods, each 19 mm dia.
10–20 m above ground: 24 rods, each 16 mm dia.
20–30 m above ground: 20 rods, each 13 mm dia.

At a level of 23 m above the ground, two defects were found; namely, one defect with a maximum adhesion ratio 0 and a circumferential length L equivalent to 17% of the full circumference, and another defect with a maximum adhesion ratio 0.5 and a circumferential length L equivalent to 23% of the full circumference. At a level of 18 m above the ground, two more defects were found; namely, one defect with a maximum adhesion ratio 0 and a circumferential length L equivalent to 64% of the full circumference, and another defect with a maximum adhesion ratio 0.3 and a circumferential length L equivalent to 20% of the full circumference.

The reduction ratio R was found to be 0.715 at 23 m above the ground and 0.22 at 18 m above the ground.

The overall bending strength Os and the elastic resistivity M of the SRC smokestack of the example were calculated by the method recommended in the "Guideline of Structural Design of Steel-reinforced Concrete Smokestack" which was worked out by THE ARCHITECTURAL INSTITUTE OF JAPAN, a Japanese juridical foundation.

Figure 9:
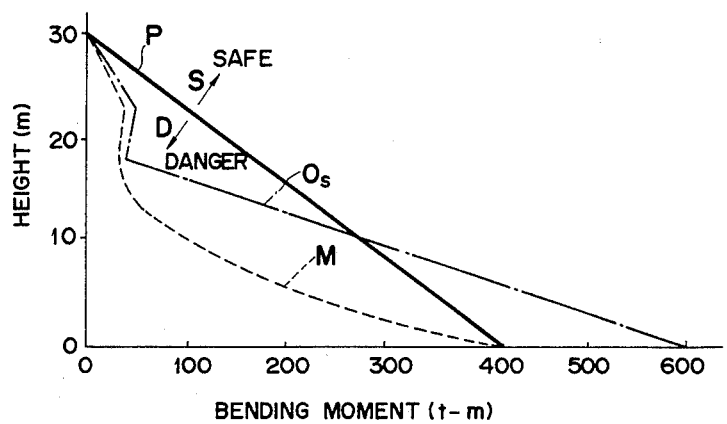
FIG. 9 is a graph showing an example of the result of diagnosis of a smokestack by the method according to the invention.

The result of the calculation is shown in FIG. 9 together with the loading P of an earthquake with an acceleration of 100 gal. As can be seen from the figure, the ultimate resistivity Os of the defect portion of the smokestack at 18 m above the ground is about 37 t-m, which is considerably lower than the seismic load of acceleration 100 gal. In fact, the smokestack may collapse at a seismic load of acceleration 22 gal (corresponding to a seismic intensity 3). This smokestack was diagnosed dangerous.

As described in detail in the foregoing, the apparatus and method for diagnosing deterioration of an SRC smokestack find defect based on an outside surface temperature distribution diagram prepared by photographing the smokestack with an infrared ray camera, determine the size of the defect, i.e., circumferential length and concrete crack width in the height direction of the smokestack, and diagnose the deterioration of the smokestack based on the defect size thus determined. Accordingly, the following outstanding effects are produced.

(1) Defects in the smokestack can be detected without touching it, and they are diagnosed in a non-destructive manner.

(2) With conventional methods of smokestack diagnosis, smoke exhaust therethrough is halted, and inspectors have to climb the smokestack for checking and diagnosing. Due to the need of time and skilled labor for such checking and diagnosing, even a dangerously defective smokestack which might collapse when exposed to a shock has been left to stand until regular check and repair time comes, for instance once a year or so. On the other hand, the apparatus and the method of the invention facilitate complete and quick diagnosis of smokestacks without requiring any interruption of smoke passage therethrough. Thus, the invention shortens the period in which dangerous smokestack is left to stand.

(3) The method of the invention is suitable for computerized diagnosis. Thus, very quick diagnosis of smokestack is possible.

What is claimed is:

1. An apparatus for diagnosing deterioration of a steel-reinforced concrete smokestack by detecting a defect in the concrete of said smokestack, comprising:
   thermal graphic means for producing a diagram of outside surface temperature distribution of said smokestack from an infrared ray photograph;
   detecting means for detecting a defect as a spot in said diagram whose temperature discontinuously differs from that of area surrounding the spot;
   means for calculating smoke temperature in the smokestack at the defect based upon the temperature difference between the inside and outside of the smokestack at the defect based in turn on the smoke temperature at the inlet of the smokestack and said outside surface temperature distribution;
   means for calculating the depth of said defect based upon said temperature difference and the temperature gradient of the wall of said smokestack;
   a means for empirically determining a concrete crack width W based on said defect depth; and
   means for assessing deterioration of strength of the smokestack based on the concrete crack width W and the area of the defect as measured on said diagram.

2. An apparatus for diagnosing deterioration of a steel-reinforced concrete (SRC) smokestack by detecting a defect in concrete of said smokestack, comprising a thermographic means for producing a diagram of outside surface temperature distribution of said SRC smokestack from an infrared ray photograph thereof, a means for detecting a defect (F) as a spot in said diagram whose temperature discontinuously differs from that of area surrounding the spot, a means for calculating smoke temperature $\theta_g$ in the smokestack at the defect by an equation $$\theta_2 = \theta_o + (K/\alpha_2 r_2)(\theta_g - \theta_o)$$

$$(1/k) = (1/\alpha_1 r_1) + (1/\alpha_2 r_2) + (1/\lambda)\ln(r_2/r_1)$$

wherein,
   $r_1$: smokestack inside radius (m)
   $r_2$: smokestack outside radius (m)
   $\theta_2$: smokestack outside surface temperature on said diagram at said area surrounding the spot with discontinuous temperature
   $\theta_f$: smoke temperature (°C.)
   $\theta_o$: outside air temperature (°C.)
   $\alpha_1$: inside surface coefficient of heat transfer
   $\alpha_2$: outside surface coefficient of heat transfer
   $\lambda$: coefficient of heat transfer concrete
   K: coefficient of overall heat transmission,
a means for calculating depth (d) of the defect (F) by an equation $$\theta_f = \theta_o \{K/\alpha_2(r_2 - d)\}(\theta_g \theta_o)$$

wherein,
   $\theta_f$: smokestack outside surface temperature on said diagram at said discontinuously different spot,
a means for empirically determining a concrete crack width (W) based on said defect depth d, and a means for assessing deterioration of strength of the smokestack based on the concrete crack width (W) and area of the defect as measured on said diagram.

3. An apparatus for diagnosing deterioration of an SRC smokestack as set forth in claim 2, wherein said area of the defect is a product of said concrete crack width (W) and a a length (L) of the defect (F) taken in a circumferential direction of the smokestack on said diagram.

4. A method of deterioration diagnosis for a steel-reinforced concrete (SRC) smokestack by detecting a defect in concrete of said smokestack, comprising steps of producing a diagram of outside surface temperature distribution of said SRC smokestack from an infrared ray photograph thereof, identifying a defect singular as a spot in said diagram whose temperature discontinuously differs from that of area surrounding the spot, calculating smoke temperature $\theta_g$ in the smokestack at the defect (F) by an equation $$\theta_2 = \theta_o + (K/\alpha_2 r_2)(\theta_g - \theta_o)$$

$$(l/K) = (1/\alpha\text{hd } 1 r_1) + (1/\alpha_2 r_2) + (1/\lambda)\ln(r_2/r_1)$$

wherein,
 $r_1$: smokestack inside radius (m)
 $r_2$: smokestack outside radius (m)
 $\theta_2$: smokestack outside surface temperature on said diagram at said are surrounding the spot with discontinous temperature
 $\theta_g$: smoke temperature (°C.)
 $\theta_o$: outside air temperature (°C.)
 $\alpha_1$: inside surface coefficient of heat transfer
 $\alpha_2$: outside surface coefficient of heat transfer
 $\lambda$: coefficient of heat transfer of concrete
 K: coefficient of overall heat transmission,
calculating depth d of the defect F by an equation $$\theta_f = \theta_o + \{K/\alpha_2(r_2 - d)\}(\theta_g - \theta_o)$$

wherein,
 $\theta_f$: smokestack outside surface temperature on said diagram at said discontinuously different spot,
empirically determining a concrete crack width (W) based on said defect depth d, and assessing deterioration of strength of the smokestack based on the concrete crack width (W) and area of the defect as measured on said diagram.

5. A method of deterioration diagnosis of an SRC smokestack as set forth in claim 4, wherein said area of the defect is represented by a product of said concrete crack width (W) and a length (L) of the defect (F) taken in a circumferential direction of the smokestack on said diagram.

* * * * *